United States Patent
Farrar et al.

(10) Patent No.: US 7,019,134 B2
(45) Date of Patent: Mar. 28, 2006

(54) AMPHOTERIC OPTICAL BRIGHTENERS, THEIR AQUEOUS SOLUTIONS, THEIR PRODUCTION AND THEIR USE

(75) Inventors: John Martin Farrar, Rawdon Leeds (GB); Andrew Clive Jackson, Harrogate (GB)

(73) Assignee: Clariant Finance (BVI) Limited, Tortola (VG)

( * ) Notice: Subject to any disclaimer, the term of this patent is extended or adjusted under 35 U.S.C. 154(b) by 183 days.

(21) Appl. No.: 10/149,952

(22) PCT Filed: Dec. 19, 2000

(86) PCT No.: PCT/IB00/01906

§ 371 (c)(1),
(2), (4) Date: Jun. 17, 2002

(87) PCT Pub. No.: WO01/46161

PCT Pub. Date: Jun. 28, 2001

(65) Prior Publication Data

US 2003/0013628 A1    Jan. 16, 2003

(30) Foreign Application Priority Data

Dec. 22, 1999   (GB) .................................. 9930247

(51) Int. Cl.
*C07D 251/68*   (2006.01)
*D06L 3/12*     (2006.01)

(52) U.S. Cl. ........................ 544/193.2; 8/119; 8/190; 8/648; 252/301.21; 252/301.23

(58) Field of Classification Search .............. 544/193.2
See application file for complete search history.

(56) References Cited

U.S. PATENT DOCUMENTS

| | | | | |
|---|---|---|---|---|
| 3,663,538 A | * | 5/1972 | Lebkucher et al. | 260/240 |
| 3,757,010 A | * | 9/1973 | Balzer et al. | 260/240 |
| 3,970,647 A | * | 7/1976 | Balzer et al. | 260/240 |
| 4,314,820 A | | 2/1982 | Weber et al. | |
| 4,478,598 A | | 10/1984 | Meyer et al. | |
| 4,888,128 A | | 12/1989 | Koll et al. | |
| 5,147,507 A | | 9/1992 | Gill | 162/158 |
| 6,426,382 B1 | | 7/2002 | Farrar et al. | 524/815 |
| 2004/0074021 A1 | | 4/2004 | Farrar et al. | |

FOREIGN PATENT DOCUMENTS

| | | |
|---|---|---|
| GB | 1 489 595 | 10/1977 |
| GB | 1313469 | 4/1979 |
| WO | WO 99/15596 | 4/1999 |
| WO | 99/67317 | 12/1999 |

* cited by examiner

*Primary Examiner*—Venkataraman Balasubramanian
(74) *Attorney, Agent, or Firm*—Tod A. Waldrop

(57) ABSTRACT

Water soluble, amphoteric optical brighteners (W) comprising at least one brightener-characteristic radical X which contain at least one anionic substituent and covalently linked over at least one tertiary amino group Z to at least one non-chromophoric, essentially aliphatic, polyquaternary ammonium-hydrocarbon radical Y containing more than one quaternary ammonium group and in which each hydrocarbon radical is optionally interrupted by and/or substituted with one or more further heteroatoms, have surprising brightening properties, especially in papermaking, and in the form of their aqueous solutions are of notable stability.

4 Claims, No Drawings

AMPHOTERIC OPTICAL BRIGHTENERS, THEIR AQUEOUS SOLUTIONS, THEIR PRODUCTION AND THEIR USE

In the production of paper it is usual to employ retention agents, dewatering agents and/or fixatives in order to improve the speed of production or other properties and yield of the product. These adjuvants are mostly of cationic character, and if it is desired to produce an optically brightened paper, care should be taken that with the use of an anionic optical brightener there does not occur a precipitation by interaction of the anionic and cationic substances. In order to avoid such an undesirable precipitation, the cationic agents are usually added at a sufficient time after the addition of the anionic component, either within a very short time range immediately before sheet formation (i.e. a few seconds before conveying the pulp to the paper sheet forming part of the assembly) or after sheet formation.

In GB-A-1489595 there is described a broad range of optical brighteners of the 4,4'-bis-(triazinylamino)-stilbene-2,2'-disulphonic acid series, containing at the triazinyl ring a defined substituent which is an amino group that contains a second nitrogen which is of amidic or basic character. If this second nitrogen is of basic character the optical brightener is amphoteric. Such amphoteric optical brighteners are however difficult to synthesize and, as the ionic character of their aqueous solutions varies with the pH, their stability may vary accordingly; the Examples of this GB-A-1489595 are all directed to optical brighteners in which said second nitrogen is of amidic character. The optical brighteners in GB-A-1489595 are described as being generically applicable to substrates of cellulose, wool, synthetic polyamide or polyurethane, including among others also paper, but they are particularly intended for the optical brightening of textile fibers and detergents.

In papermaking there are still usually employed anionic optical brighteners, mainly of the 4,4'-bis-(triazinylamino)-stilbene-2,2'-disulphonic acid series, one typical representative being an optical brightener of the formula

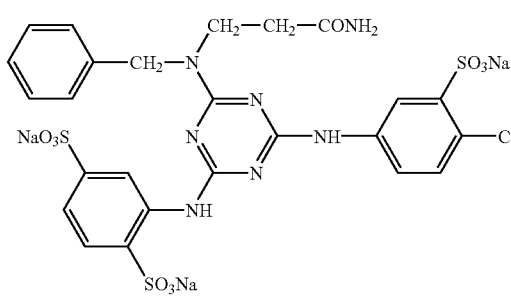

which is in particular employed in the size press.

It has now surprisingly been found that certain amphoteric products with optical brightening properties, as defined below, especially in aqueous solution, more particularly in concentrated aqueous solution, are valuable multi-functional agents that combine the activity of optical brighteners and of cationic adjuvants—especially if they are of polymeric character—(e.g. as retention assistants, drainage assistants or fixative in paper production), which in the production of optically brightened paper allows the addition of optical brightener at any time before, during or after sheet formation. Further they are also of unexpected compatibility with anionic adjuvants used in papermaking. Furthermore it has also surprisingly been found that aqueous solutions of these amphoteric optical brighteners are of unexpected stability.

The invention relates to the defined amphoteric optical brighteners and their aqueous solutions, and to their production and use.

The invention thus provides a water soluble, amphoteric optical brightener (W) comprising at least one brightener-characteristic radical X of an anionic optical brightener of the 4,4'-bistriazinylaminostilbene-2,2'-disulphonic acid series which contains the group of formula

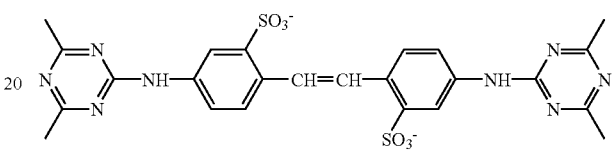

and is covalently linked over at least one tertiary amino group Z to at least one non-chromophoric, essentially aliphatic, poly(quaternary ammonium)-hydrocarbon radical Y containing more than one quaternary ammonium group and in which each hydrocarbon radical is optionally interrupted by and/or substituted with one or more further heteroatoms.

These amphoteric optical brighteners may thus also be represented as essentially consisting of constituent units of the average formula $$X'\text{-}Z\text{-}Y' \qquad (I_W),$$

in which

X' signifies one equivalent of X, i.e. X divided by its covalent valence, and

Y' signifies one equivalent of Y, i.e. Y divided by its covalent valence.

As brightener-characteristic radical X there is meant the essential structural component of conventional optical brighteners of the 4,4'-bistriazinylaminostilbene-2,2'-disulphonic acid series, containing the characteristic conjugation system which provides the typical UV-light absorption and fluorescence properties of the optical brightener.

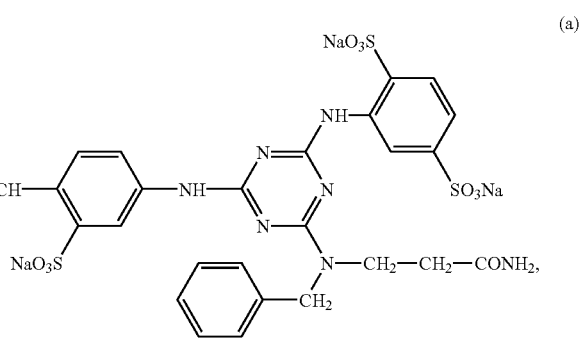

Further the optical brightener radical X contains anionic substituent, in particular as otherwise conventionally present in anionic optical brighteners of the 4,4'-bistriazinylaminostilbene-2,2'-disulphonic acid series, mainly sulphonic acid groups and optionally carboxylic acid groups, which preferably are in salt form. The optical brightener radical may be the radical of any anionic optical brightener of the 4,4'-bistriazinylaminostilbene-2,2'-disulphonic acid series, which contains the characteristic group of formula (x).

The poly(quaternary ammonium)-hydrocarbon radicals Y preferably contain further heteroatoms, more preferably oxygen in the form of ether bridges and/or hydroxy groups. The poly(quaternary ammonium)-hydrocarbon radicals Y may optionally be crosslinked to higher polymeric forms.

The water soluble, amphoteric optical brighteners (W) of the invention may be produced by means of addition and condensation reactions of a kind conventional per se, in particular by reacting under dehydrohalogenating conditions an optical brightener precursor that contains at least one reactive halogen, with a suitable, corresponding secondary amine that contains more than one quaternary ammonium group and/or with a corresponding non-quaternary precursor thereof and then quaternizing the reaction product. More particularly the process for the production of the amphoteric optical brighteners of the invention is characterised in that an optical brightener precursor (B) of formula $$X\text{-}(Hal)_m \qquad (I),$$

wherein

Hal signifies halogen, preferably chlorine, and m signifies an integer in the range of 1 to 4, is reacted under dehydrohalogenating conditions with an amine ($P_A$) of formula

 $\text{-Y''}$      (II), wherein

Y" has the significance of Y or signifies a non-quaternary precursor of Y,

Z" has the significance of Z if Y" has the significance of Y or, if Y" is a non-quaternary precursor of Y, is a group of formula —$NR_0$— in which $R_0$ is a low molecular aliphatic radical which is optionally substituted with hydroxy, nitrile or carbamoyl and is optionally interrupted by oxygen, or is a bond to Y", and n signifies the number of reactive tertiary amino groups linked to Y" and is at least 1, and, if Y" is a non-quaternary precursor of Y, it is further reacted with a reactant (Q) suitable for introducing at least one quaternary ammonium group and/or quaternizing at least one quaternizable amino group.

As optical brightener precursor especially of formula (I) there may be employed any conventional intermediate as typically employed for producing corresponding anionic optical brighteners of the bistriazinylaminostilbene disulphonic acid series, e.g. of the formula

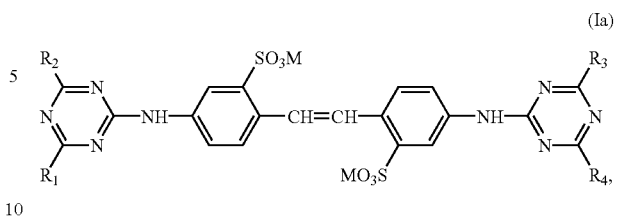

wherein $R_1$, $R_2$, $R_3$ and $R_4$ signify, independently from each other, the radical of an amine or of an alcohol, and M signifies hydrogen, low molecular ammonium or an alkali metal cation, In the significances of $R_1$, $R_2$, $R_3$ and $R_4$ the radical of an alcohol is usually the radical of an aliphatic alcohol or of a phenol. The radical of the aliphatic alcohol is mostly $C_{1-4}$-alkoxy, the phenol radical is mostly unsubstituted phenoxy. The amine radical is e.g. optionally substituted anilino or an aliphatic aminogroup —$NR_0'R_0''$, wherein $R_0'$ signifies hydrogen, $C_{1-4}$-alkyl, benzyl, $C_{2-3}$-hydroxyalkyl or carboxy-($C_{1-4}$-alkyl), $R_0''$ signifies hydrogen, $C_{1-4}$-alkyl, $C_{2-3}$-hydroxyalkyl, sulpho-$C_{1-3}$-alkyl, sulpho-$C_{3-4}$-hydroxyalkyl, cyano-($C_{1-3}$-alkyl), carbamoyl-($C_{1-3}$-alkyl), carboxy-($C_{1-4}$-alkyl), carboxy-[cyano-($C_{2-3}$-alkyl)], carboxy-[carbamoyl-($C_{2-3}$-alkyl)] or dicarboxy-($C_{2-3}$-alkyl), or $R_0'$ and $R_0''$ together with the nitrogen to which they are linked form a heterocycle, $R_1$ and $R_3$ preferably signify an optionally substituted anilino group of formula

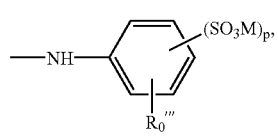

wherein $R_0'''$ signifies hydrogen, methyl, methoxy or chlorine, preferably hydrogen, and p signifies 0, 1 or 2, or an aliphatic aminogroup —$NR_0'R_0''$, $R_0'$ preferably signifies $C_{1-2}$-alkyl, benzyl, $C_{2-3}$-hydroxyalkyl or carboxy-($C_{1-2}$-alkyl).

$R_0''$ preferably signifies $C_{2-3}$-hydroxyalkyl, carbamoyl-($C_{1-3}$-alkyl), cyano-($C_{1-3}$-alkyl) or carboxy-($C_{1-2}$-alkyl).

If $R_0'$ and $R_0''$ together with the nitrogen to which they are linked form a heterocycle, this is preferably a morpholine ring or a carboxypyrrolidine ring, $R_2$ and $R_4$ preferably signify methoxy, phenoxy or more preferably an aliphatic aminogroup —$NR_0'R_0''$, The two symbols $R_1$ and $R_3$ in formula (I) may have the same significance or different significances. Preferably they have the same significance.

Similarly also the two symbols $R_2$ and $R_4$ in formula (I) may have the same significance or different significances. Preferably they have the same significance.

The corresponding precursors within the scope of formula (I) may be represented by the formula

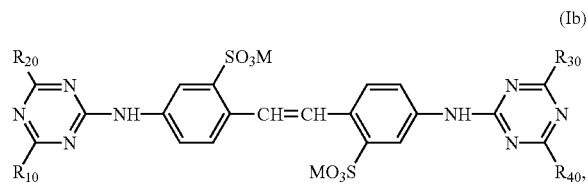

(Ib)

wherein
$R_{10}$, $R_{20}$, $R_{30}$ and $R_{40}$, independently from each other, signify chlorine or have one of the significances of $R_1$, $R_2$, $R_3$ or $R_4$ respectively, with the proviso that at least one of $R_{10}$, $R_{20}$, $R_{30}$ and $R_{40}$ signifies chlorine.

Preferred optical brightener precursors of formula (Ib) are those in which two of $R_{10}$, $R_{20}$, $R_{30}$ and $R_{40}$, more preferably $R_{20}$ and $R_{40}$ signify chlorine, especially those in which $R_{10}$ and $R_{30}$ signify each a radical of formula (a). Particularly preferred precursors of formula (Ib) may thus be represented by the following formula or a combination of both, and the other being
($A_2$) a mono-primary amine which on reaction with the chlorine of the adduct gives a secondary aminogroup, so that this product is capable of reacting by means of the secondary aminogroup with a halogen of the optical brightener precursor (B).

The epichlorohydrin-derived condensates are preferably polyquaternary, and may be crosslinked polymers obtainable by an at least three-stage synthesis, in which in the first stage epichlorohydrin is reacted with a hydroxy compound to give a chloroterminated adduct; in the second stage the chloroterminated adduct is reacted with an amine suitable for introducing a quaternary ammonium group, in particular—for the production of crosslinked products—a secondary amine or an at least bifunctional tertiary amine, leaving some terminal chlorine unreacted for further reaction with the primary amine ($A_2$); and in the third stage ($A_2$) is reacted with this chlorine.

As starting hydroxy compounds there may be employed preferably fully aliphatic compounds, e.g. mono- or oligofunctional alcohols.

Suitable hydroxy compounds are bi- to hexa-functional aliphatic alcohols with up to six, preferably three to six, carbon atoms in the hydrocarbon radical, in particular of the following formula $$R{-}(OH)_{x1} \qquad (III),$$

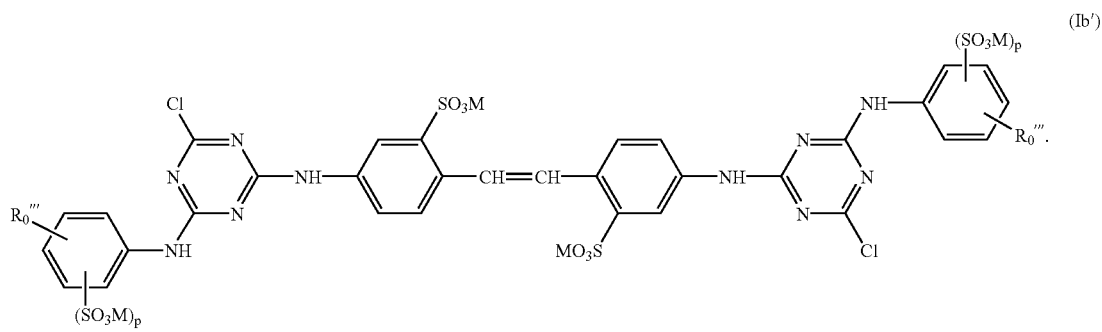

The reactant for introducing the polyquaternary ammonium-hydrocarbon radicals Y (linked over Z) is in particular a secondary amine that preferably already contains a corresponding number of quaternary ammonium groups, and preferably contains further heteroatoms, preferably oxygen atoms Preferably this reactant, which above is represented by means of formula (II), is an oligocondensate of a chloroterminated adduct of epichlorohydrin to an aliphatic oligohydroxy compound with two species of amines (A), the one being amines ($A_1$), i.e.

($A_1'$) a monoamine suitable for introducing a quaternary ammonium group or ($A_1''$) a diamine or higher functional optionally further substituted polyamine in which the aminogroups are tertiary aminogroups and which does not contain any primary or secondary amino groups, suitable for introducing one or more quaternary ammonium groups in which
R signifies the x1-valent radical of a $C_{3-6}$-alkane and
x1 signifies a number from 3 to the number of carbon atoms in X, or a mixture of oligohydroxyalkanes of formula (III), or a mixture one or more oligohydroxyalkanes of formula (III), with a $C_{2-3}$-alkanediol, or polyalkyleneglycols, in particular of the average formula $$HO\text{-}(Alkylene\text{-}O)_{x2}\text{-}H \qquad (IV),$$

wherein
Alkylene signifies $C_{2-4}$-alkylene and
x2 signifies a number from 2 to 40.

Preferred compounds of formula (Va) are those of formula $$H—(CHOH)_{x3}—H \tag{III'}$$

with x3 being 3 to 6.

Alkylene in formula (IV) is ethylene, propylene and/or butylene and the polyalkyleneglycols of formula (IV) may be homo- or copolymers, preferably water soluble products (with a solubility in water of at least 10 g/l at 20° C. and pH 7). As polyalkyleneglycols of formula (IV) there are preferably employed polyethyleneglycols or copolyalkyleneglycols containing a prevailing molar proportion of ethyleneoxy-units. More preferably there are employed polyethyleneglycols, i.e. compounds of formula (IV) in which Alkylene signifies only ethylene.

By the reaction of the hydroxy groups with the epichlorohydrin the epoxy ring of the epichlorohydrin is opened and a corresponding adduct is formed which contains a 2-hydroxy-3-chloropropyl-1 radical. This reaction is preferably carried out in the absence of any other solvent and, especially for hydroxy, in the presence of a catalyst, which is e.g. a Lewis acid, preferably boron trifluoride e.g. in the form of its etherate or acetic acid complex. This reaction is exothermic and the epichlorohydrin reacts with the available hydroxy groups and, as reaction proceeds, may also react with a hydroxy group of a 2-hydroxy-3-chloropropyl-1 radical formed during the reaction, so that some of the hydroxy groups in a polyfunctional starting reactant [e.g. of formula (III)] may even remain non-reacted. Depending on the molar ratio, on the functionality of the starting hydroxy-compound and on its configuration—especially if x1 in formula (III) is 4 to 6—the degree of reaction of the x1 OH groups with epichlorohydrin may vary, and may e.g. be in the range of 15 to 95%, mostly 30 to 90%, of the total number of OH groups originally present in the starting polyol. The obtained adduct is a chloro-terminated product.

The chloroterminated adduct is then reacted with a suitable amine to produce a polyquaternary optionally crosslinked product, e.g. with a simple tertiary amine or with a crosslinking reactant that is capable of providing a bridging quaternary ammonium group, which suitably is a tertiary oligoamine or a secondary monoamine. Such amines preferably correspond to the following formula

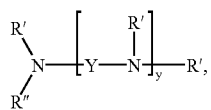

(V)

in which

Y signifies $C_{2-3}$-alkylene, y signifies a number from 0 to 3,

R' signifies $C_{1-3}$-alkyl or $C_{2-3}$-hydroxyalkyl and

R" has a significance of R', if y is 1 to 3, or signifies hydrogen, if y is 0, especially as a reactant leading to a crosslinking, where the starting oligohydroxycompound is of formula (III), or to the formula $$N(R')_3 \tag{VI},$$

wherein
  each symbol R' has the above indicated significance, or the three symbols R' together with the nitrogen to which they are linked, form a pyridine or methylpyridine ring, or

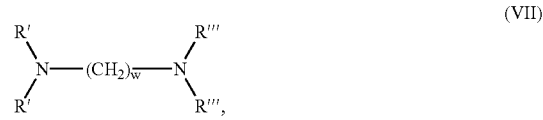

wherein
  R''' signifies $C_{1-3}$-alkyl
and
  w signifies a number from 2 to 6, the amines of formulae (VI) and (VII) being especially suitable as reactants, where the starting oligohydroxycompound is of formula (IV).

For an optional chain-terminating, quaternizing reaction there may e.g. be employed a tertiary monoamine preferably of formula (VI).

As amino compounds of formula (V) there may be employed known amines. The $C_{1-3}$-alkyl radicals in R' and R" may be methyl, ethyl, propyl or isopropyl, the lower molecular ones being preferred, especially methyl. The $C_{2-3}$-hydroxyalkyl radicals are preferably 2-hydroxyethyl or -propyl. Among the $C_{1-3}$-alkyl radicals and the $C_{2-3}$-hydroxyalkyl radicals the $C_{1-3}$-alkyl radicals are preferred, especially methyl. The index y may be any number from 0 to 3 preferably 0 to 2, more preferably 0 or 1. Representative amines of formula (V) are dimethylamine, diethanolamine, tetramethylethylenediamine, tetramethylpropylenediamine, N,N-diethanol-N',N'-dimethylethylenedamine, pentamethyldiethylenetriamine and hexamethyltriethylenetetramine, among which the difunctional amines, in particular the lower molecular ones, are preferred, especially dimethylamine and tetramethylethylenediamine. Representative amines of formula (VI) are trimethylamine, triethylamine, dimethylethanolamine, methyldiethanolamine, triethanolamine and pyridine, among which trimethylamine and triethylamine are preferred. In formula (VII) the index w preferably is 2 or 3. Representative amines of formula (VII) are tetramethylethylenediamine, tetramethylpropylenediamine and N,N-diethanol-N',N'-dimethylethylenediamine.

Suitable monoprimary amines ($A_2$) are for instance mono-$C_{1-4}$-alkyl-amines optionally substituted with hydroxy, methoxy, tertiary amino, —CN or —CONH$_2$, e.g. mono-$C_{2-4}$-hydroxyalkyl-amines, mono-methyl-amine, mono-ethyl-amine, mono-isopropyl-amine, mono-ethanol-amine, mono-isopropanol-amine, N,N-dimethylaminopropylamine and N,N-diethanolaminopropylamine.

The polycationic polyquaternary products may be polymers at least insofar as the reaction with the amine may lead to a polymer or the starting product is polymeric (e.g. is a polyalkylene glycol) or both.

The molar ratio of quaternizing amine to epichlorohydrin adduct is suitably chosen so that a polyquaternary intermediate product is produced which has at least one unreacted chlorine available in the molecule for reaction with the primary amine.

Suitable monoprimary amines ($A_2$) correspond e.g. to the following formula

$$H_2N\text{-Alkylene-G} \qquad (VIII),$$

wherein
Alkylene signifies $C_{2-4}$-alkylene
and
G signifies hydrogen, $C_{1-2}$-alkoxy, CN, $CONH_2$ or $-N(R')_2$.

The molar ratio of quaternizing amine to epichlorohydrin adduct of a compound of formula (III) may e.g. be chosen so that for every mole-equivalent of adduct (with reference to chlorine) there is employed 0.1 to 0.3 moles of amine ±30%, e.g. ±10%, if the reaction is a crosslinking or up to twice this quantity if the reaction is not a crosslinking. The molar ratio of quaternizing amine to epichlorohydrin adduct of a compound of formula (IV) may e.g. be chosen so that for every mole-equivalent of adduct (with reference to chlorine) there is employed 0.6 mole of amine of formula (VII) ±30%, e.g. ±10%, if the reaction is a crosslinking or up to twice this quantity if the reaction is not a crosslinking. The molar ratio of quaternizing amine to epichlorohydrin adduct of a compound of formula (IV) may e.g. be chosen so that for every mole-equivalent of adduct (with reference to chlorine) there is employed 0.4 mole of amine of formula (VI) ±40%, e.g. ±20%. Depending on the chosen reaction components and conditions and on the envisaged product, a preferred or optimum ratio may be chosen by means of a few preliminary tests.

The non-reacted chlorines of the product are reacted with the primary amine, preferably to at least 70%, more preferably exhaustively.

The concentration of the reactants is preferably chosen in such a way that the concentration of $(P_A)$ in the aqueous mixture is in the range of 10 to 75%, preferably 20 to 70% by weight.

The reaction of quaternizing amine with the adduct is carried out preferably in aqueous medium and preferably with heating, e.g. at a temperature in the range of 50 to 100° C., preferably 60 to 90° C. During the reaction, at least at the beginning, the basicity of the amine is sufficient for the quaternizing alkylation of the amine with the adduct, i.e. with the chloride used as an alkylating agent. The pH of the reaction mixture is preferably in the range of 4 to 9, at the beginning being preferably in the range of 7 to 9. As reaction proceeds, the alkalinity of the mixture and the concentration of crosslinking amine diminish. If in the reaction product there is present a proportion of covalently linked chlorine which is higher than desired, there may e.g. be added a further reactant which is a monofunctional tertiary amine and/or, if the starting crosslinking reactant is a secondary monoamine, there may be added a suitable strong base, such as an alkali metal hydroxide, preferably sodium hydroxide, so that the pH is preferably maintained in the range of 7 to 9. When the reaction with the first species of amines, i.e. quaternising, has completed or has reached the desired degree, the second species, i.e. the primary amine, is added and reaction is continued. If desired, when also this reaction has completed, the reaction mixture may be acidified by addition of a conventional acid, preferably a mineral acid (such as hydrochloric acid, sulphuric acid or phosphoric acid) or a low molecular aliphatic carboxylic acid e.g. with 1 to 6 carbon atoms (such as formic acid, acetic acid, citric acid or lactic acid), e.g. to reach a pH below 7, more preferably in the range of 4 to 7, most preferably in the range of 5 to 6.5. Usually such an acidification is however not necessary. If quaternization is carried out with crosslinking, the progress of the crosslinking reaction may be followed by checking the viscosity of the reaction mixture, which gives an empirical impression of the degree of crosslinking. A suitable viscosity is e.g. in the range of 200 to 3000 cP. According to a preferred feature of the process, the quaternization is carried out without crosslinking.

The reaction with the primary amine is carried out preferably with stirring and heating, for instance at a temperature in the range of 50 to 120° C., preferably 60 to 100° C. The reaction is advantageously carried out with the aid of a dehydrochlorinating adjuvant, in particular a base, preferably alkali metal hydroxide carbonate or bicarbonate.

The reaction of $(P_A)$ with the optical brightener precursor (B) may be carried out at temperatures and pH ranges as usually suitable for reacting the respective halogens, in particular chlorine atoms, of the above precursors, for instance at temperatures in the range of 20 to 100° C. and at pH values in the range of 4 to 10, depending on the number of chlorine atoms in particular; for instance if in formula (Ib) all four of $R_{10}$, $R_{20}$, $R_{30}$ and $R_{40}$ signify chlorine, two of them may be reacted under acidic to neutral conditions (e.g. pH 4 to 7) and at temperatures in the range of 20 to 50° C., while the two further chlorine atoms may then be reacted under stronger reaction conditions, e.g. at pH values in the range of 6 to 10 and at temperatures in the range are 40 to 100° C. Where (B) contains two or more reactive halogen atoms, the resulting product (W) may, if desired, also be correspondingly chain-extended or/and (further) crosslinked.

The obtained aqueous composition of (W), i.e. $(W_A)$, is an aqueous solution, i.e. a true or at least colloidal solution, in which preferably the sulpho groups are in salt form, more preferably non-inner salt form; the pH of $(W_A)$ is preferably basic, e.g. up to pH 10, advantageously in the range of pH 7.5 to 9.5. The viscosity of the solution of (W) may e.g. be in the same range as above, i.e. in the range of 200 to 3000 cP. $(W_A)$ may be used directly as produced, in particular in the concentrated form as produced, or—if desired—it may be modified in salt content and/or concentration e.g. by membrane filtration, and/or it may be combined with any further desired components, in particular with an additive that protects the composition against any harmful influence of microorganisms, e.g. with an additive that stops the growth of disturbing microorganisms or with a biocide, e.g. as commercially available, and in a concentration as usually reccommended for such additives, e.g. in a concentration of 0.001 to 0.1% by weight referred to the liquid composition. The (W)-content of the concentrated aqueous solutions $(W_A)$ may range in a broad scope and it is possible to prepare highly concentrated solutions, e.g. of a (W)-concentration of up to 80% by weight, e.g. in the range of 20 to 80% by weight, preferably 30 to 80% by weight.

The so produced compositions combine the properties of component (B) as an optical brightener and of the cationic component $(P_A)$, which may e.g. be an internal or external functional additive in papermaking, for instance a flocculant, drainage assistant, retention adjuvant or a fixative, or may just otherwise modify the optical brightener, and provide an amphoteric product of surprising properties and compatibility at any stage of paper production and also in sizes and coatings. The (W) composition $(W_A)$ of the invention provides in particular the possibility of adding the anionic optical brightener at any time before, during or after formation of the paper web or sheet. This means that the multifunctional composition of the invention may be added also in the aqueous stock, without it being necessary to immediately make the paper sheet.

The amphoteric products (W) of the invention are also compatible with other cationic additives or components that might be present or added in the stock, e.g. retention aids and/or cationic surfactants.

A particular feature of the invention is thus represented also by the process for the production of optically brightened paper wherein an aqueous (W)-solution as defined above is employed as a functional internal or external additive, optionally in the presence of other cationic additives.

The amphoteric products (W) of the invention, expediently in the form of an aqueous composition ($W_A$) as produced by the method described above, may thus serve simultaneously as assistants in the production of paper, in particular as fixatives, for reducing the amount of backwater components, e.g. turbidity, in backwaters (white waters) from paper production, and as optical brighteners for producing optically brightened paper.

The invention thus provides also a method for producing paper, in partticular a paper web or sheet, from aqueous stock, wherein (W) is employed as an adjuvant, especially as a fixative. As "paper" there is intended herein also paper board and cast paper shapes. As an aqueous stock there is intended any stock, in particular cellulosic stock, as employed for papermaking and wherein the pulp suspension may derive from any origin as conventionally employed for papermaking, e.g. virgin fiber (chemical or mechanical pulp), machine broke (in particular coated broke) and reclaimed paper (especially deinked and optionally bleached reclaimed paper). The aqueous paper pulp or stock may also contain further additions as may be desired for a certain quality, such as sizing agents, fillers, flocculating agents, drainage and/or retention assistants, which are preferably added after the addition of (W). The stock concentration may vary in any conventional range as suitable for the employed pulp, machine, process and desired paper quality, e.g. in the range of 0.4 to 10%, preferably 0.8 to 6%, by weight of dry pulp. According to a particular feature of the invention there is employed a pulp from coated broke and/or bleached, deinked reclaimed paper optionally blended with other pulp.

The amphoteric polycationic products (W) are preferably employed in a concentration in the range of 0.05 to 0.5% by weight, more preferably 0.1 to 0.4% by weight referred to dry pulp. The pH may be in the weakly basic to distinctly acidic range, preferably in the range of pH 4 to pH 8, more preferably pH 5 to pH 7. The paper may be produced using any conventional paper making machines and in a manner conventional per se. The resulting backwater is of reduced contaminants content, in particular of reduced turbidity, and consequently the respective BOD and/or COD values are also reduced. By the use of (W) there may also be achieved an improvement of the efficiency of other cationic wet-end additives such as flocculants, retention assistants or drainage assistants, and there may be obtained paper of optimum quality while the occurrence of paper breakings due to disturbing anionic contaminants is correspondingly reduced, while the efficiency of the optical brightener is optimal and there is obtainable paper of very regular whiteness in high yield. The so produced paper may in particular be employed as a substrate for ink-jet-printing.

The amphoteric optical brighteners of the invention may be applied in any stage and composition for papermaking, in particular also in aqueous size compositions and in coating pastes, and thus the invention provides also an aqueous paper size composition comprising an amphoteric optical brightener (W) of the invention and conventional further paper size components, and furthermore the invention provides also an aqueous paper coating paste comprising an amphoteric optical brightener (W) of the invention and conventional further coating paste components, especially fillers and/or pigments and optionally a resin and/or binder and optionally a surfactant, where these conventional components may in particular be employed in concentrations as otherwise usually employed in size or coating compositions.

It has further surprisingly been found that by cationically modifying the inorganic pigments or fillers with the amphoteric products (W) or respectively their aqueous composition ($W_A$) products as defined above, there may be achieved products of notable properties e.g. in the brightness of the inorganic products, or in the physical form of the treated inorganic substances, such as workability and regular distribution in suspension.

The invention thus also provides a cationically modified white pigment ($W_P$) in particulate form, essentially consisting of a particulate inorganic white pigment (M) of a particle size in the range of 0.1 to 40 μm and an applied amphoteric product (W).

The invention thus more particularly concerns the stated modification of particulate inorganic white pigments (M) by (W) to the cationically modified products ($W_P$).

(M) comprise in general known inorganic substances as usually employed as white pigments or fillers (or loading agents), and which more particularly are conventionally employed in non-coloured form especially in papermaking, and as may also be employed in other fields of technique such as paints, lacquers, cosmetics, plastics, construction material etc. Mainly concerned are those for papermaking, since in papermaking industry problems exist with the quenching of optical brightening agents by additives used to improve retention and drainage during the papermaking process.

The term "pigment" as used herein is intended to comprise also the term "filler", insofar as a same substance may be used as filler or pigment.

The inorganic pigment (M) may be any such substance, naturally occurring and optionally physically modified, or synthetically produced, and preferably as employed in particular in paper coatings or as fillers or loading agents in the paper sheet, as added e.g. in the size or also in the paper pulp suspension. (M) may include mineral substances and synthetically produced inorganic substances, such as silica, alumina, titanium dioxide, zinc oxide and sulphide, and inorganic salts, e.g. silicates, aluminates, titanates, sulphates and carbonates, of low valence metal ions, mainly of alkali metal ions, alkaline earth metal ions or earth metal ions, especially of sodium, potassium, magnesium, calcium, barium and/or aluminium. The following may be mentioned as examples: titanium dioxides (rutile, anatase), potassium titanates, zinc oxide, zinc sulphide, lithopone, calcium sulphates (gypsum or anhydrite), various forms of silica (e.g. amorphous silica such as diatomite), alumina trihydrate, sodium silico-aluminate, talc ($MgO.4SiO_2.H_2O$), barium sulphate (baryte, blanc fixe), calcium sulphoaluminate (satin white), chrysotile, china clay in various degrees of whiteness (mainly comprising $Al_2O_3.SiO_2.H_2O$ and optionally further metal oxides such as iron oxide, titanium dioxide, magnesium oxide, calcium oxide, sodium oxide and/or potassium oxide) and calcium carbonate in various forms (mineral natural form or synthetic precipitated and/or crystallised forms). They may be employed in the forms as commercially available, in particular of various degrees of whiteness, e.g. of a whiteness >80, mostly >82 (measured according to ISO methods), but also less white products may be used, e.g. of a whiteness $\leq 82$, or even $\leq 80$, e.g. in the range of 70 to 80.

The particle size of (M) is on average in the range of 0.1 to 40 μm, as obtainable by conventional methods, e.g. by grinding and/or milling and/or—if required—sieving and screening, or by suitable precipitation and/or (micro)crystallisation methods. Commercially available products mostly contain in general a certain proportion of particles smaller than 0.1 μm (dust) and/or some granules larger than 40 μm; preferably these larger size components are $\leq 20\%$ by weight, more preferably $\leq 10\%$ by weight. Preferably the average particle size of such inorganic pigments (M) is within the range of 0.1 to 20 μm, more preferably 0.2 to 10 μm, most preferably 0.2 to 5 μm, preferably at least 75%, preferably ≧80% of the particles being within these ranges. Among the mentioned pigments (M) are preferred those comprising silicates, in particular kaolin, and especially those comprising carbonates, in particular calcium carbonates.

The inorganic pigment (M) may comprise a conventional dispersant or wetting agent as commercially available, on its surface, e.g. polyphosphates, in a suitable low concentration as usual e.g. <0.5% by weight, preferably <0.3% by weight. For the purpose of the invention the presence of such a surfactant is not essential and (M) may also be exempt of a dispersant or wetting agent.

As mentioned above, (M) may be employed in the forms as commercially available, in particular it may be employed in dry form or in the form of a concentrated aqueous slurry, e.g. with a solids content in the range of 40 to 70% by weight.

Preferred pigments and fillers (M) have e.g. a specific surface area in the range of 5 to 24 $m^2$/g, preferably 7 to 18 $m^2$/g.

For the production of the cationically modified pigment $(W_P)$ (M) may thus be mixed with $(W_A)$.

According to a further variant a solution of $(W_A)$, may be sprayed on a dry (M)-powder with mixing.

The produced aqueous $(W_P)$-suspension may, if desired, be filtered and dried to a white pigment $(W_P)$ in dry, particulate form of corresponding particle size. If desired it may be agglomerated to larger agglomerate particles, e.g. by compaction e.g. to granules, pellets or tablets.

The invention thus also provides a process for the production of a white pigment $(W_P)$ in the form of an aqueous suspension, wherein an aqueous supension of (M) is admixed with $(W_A)$ and also a process for the production of a white pigment $(W_P)$ in dry form, wherein an aqueous supension of (M) is admixed with $(W_A)$, the suspension is filtered and the residue is dried and optionally compacted.

This process is in particular carried out substantially in the absence of further functional additives that would interfere in a disturbing way with the reaction, in particular in the absence of other functional papermaking additives and components (such as resins, fibres and/or paper-size components).

The weight ratio of (W) to (M) may range broadly, depending on the desired degree of cationic modification of (M) in $(W_P)$; it may e.g. range in the scope of 0.01:100 to 10:100, preferably 0.2:100 to 5:100, more preferably 0.3:100 to 4:100. For compacted dry forms this weight ratio is preferably in the range of 0.01:100 to 3:100, more preferably 0.2:100 to 2:100.

(W) may be applied in the form of an aqueous solution—e.g. of a concentration in the range 0.1 g/l to the saturation limit—to (M) by any suitable method. If (M) is used in the form of an aqueous slurry, $(W_A)$ is preferably a concentrated solution—e.g. of a concentration in the range 1 g/l to the saturation limit, preferably in the range of 5 g/l to 40 g/l—and may be mixed with it in the desired proportion e.g. by plain stirring and optionally with heating or cooling, e.g. at a temperature in the range of 5 to 60° C., preferably 10 to 40° C., more preferably with slight heating e.g. in the temperature range of 25 to 40° C. or at ambient conditions without any heating or cooling. If (M) is in the dry form, a sprayable, preferably more diluted solution of (W)—e.g. of a concentration in the range of 0.1 to 20 g/l, preferably 0.5 to 10 g/l—may e.g. be applied by spraying and mixing, optionally with heating or cooling, e.g. at a temperature in the range of 5 to 60° C., preferably 10 to 40° C., more preferably with slight heating e.g. in the temperature range of 25 to 40° C. or at ambient conditions without any heating or cooling.

The pH of the solution $(W_A)$ may range broadly, e.g. from the weakly acidic to weakly basic range, in particular from pH 5 to pH 8, preferably pH 5.5 to pH 7.5.

According to the invention there may be produced amphoteric optical brightener solutions, namely $(W_A)$, of high stability and of notable performance properties, in particular in the production of optically brightened paper and in the treatment of inorganic white pigments or fillers, especially in degree of whiteness and yield.

In the following Examples parts and percentages are by weight, if not otherwise indicated; parts by weight relate to parts by volume as grams to milliliters; the temperatures are indicated in degrees Celsius; in Application Examples C and D °SR signifies degrees Schopper-Riegler and the percentages relate to the weight of the starting aqueous pulp suspension.

EXAMPLE 1

Amphoteric Optical Brightener 1

A mixture of 35.2 parts D-sorbitol and 17.8 parts glycerol is heated to 90° C. until a solution forms. The stirred solution is cooled to 80° C., and treated with 0.25 parts boron trifluoride-acetic acid complex. Stirring is continued at 80° C. for 10 minutes until the catalyst is fully dispersed. To the stirred mixture is then added 136.4 parts of epichlorohydrin over 1 hour at 80–85° C. Once addition is complete, the reaction mixture is cooled to 30° C., treated with 99.8 parts N,N-dimethylethanolamine and heated at 90° C. for 3 hours. The reaction mixture is then further treated with 17.1 parts ethanolamine at 90° C. for 2 hours to give a water-miscible, cationic intermediate (1c).

The intermediate (1c) is stirred at 50–60° C. and treated with 100.7 parts of the optical brightener precursor of formula (1a),

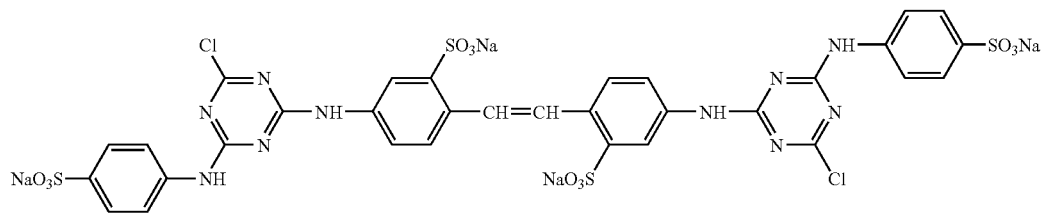

(1a)

in the form of a 20% aqueous suspension, and 18.1 parts sodium bicarbonate. The reaction mixture is heated to reflux for 4 hours to give an aqueous solution of the amphoteric optical brightener 1, which can be used as is.

EXAMPLE 2

Amphoteric Optical Brightener 2

A mixture of 35.2 parts D-sorbitol and 17.8 parts glycerol is heated to 90° C. until a solution forms. The stirred solution is cooled to 80° C., and treated with 0.25 parts boron trifluoride-acetic acid complex. Stirring is continued at 80° C. for 10 minutes until the catalyst is fully dispersed. To the stirred mixture is then added 64.2 parts of epichlorohydrin over 1 hour at 80–85° C. Once addition is complete, the reaction mixture is cooled to 30° C., treated with 50.0 parts triethylamine and heated at 90° C. for 3 hours. The reaction mixture is then further treated with 12.4 parts isopropanolamine at 90° C. for 2 hours to give a water-miscible, cationic intermediate (2c).

The intermediate (2c) is stirred at 50–60° C. and treated with 86.2 parts of the optical brightener precursor of formula (2a)

The intermediate (3c) is stirred at 50–60° C. and treated with 102.8 parts of optical brightener precursor (1a), in the form of a 20% aqueous suspension. The reaction mixture is heated to 95–100° C. for 4 hours at pH 8 (30% sodium hydroxide) to give an aqueous solution of the amphoteric brightener 3 which can be used as is.

EXAMPLE 4

Amphoteric Optical Brightener 4

A mixture of 35.2 parts D-sorbitol and 17.8 parts glycerol is heated to 90° C. until a solution forms. The stirred solution is cooled to 80° C., and treated with 0.25 parts boron trifluoride-acetic acid complex. Stirring is continued at 80° C. for 10 minutes until the catalyst is fully dispersed. To the stirred mixture is then added 106.0 parts of epichlorohydrin over 1 hour at 80–85° C. Once addition is complete, the reaction mixture is cooled to 30° C., treated with 56.5 parts N,N-dimethylethanolamine and heated at 90° C. for 2 hours. The reaction mixture is then sequentially treated with 21.0 parts N,N,N',N'-tetramethylethylene diamine for 2 hours at 90° C. and with 5.6 parts ethanolamine for 2 hours at 90° C. to give a water-miscible, cationic intermediate (4c).

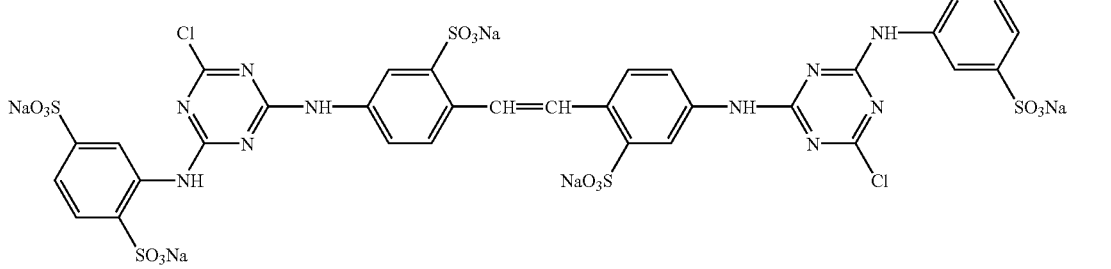

in the form of a 30% aqueous suspension, and 12.9 parts sodium bicarbonate. The reaction mixture is heated to reflux for 4 hours to give an aqueous solution of the amphoteric optical brightener 2 which can be used as is.

EXAMPLE 3

Amphoteric Optical Brightener 3

A mixture of 35.2 parts D-sorbitol and 17.8 parts glycerol is heated to 90° C. until a solution forms. The stirred solution is cooled to 80° C., and treated with 0.25 parts boron trifluoride-acetic acid complex. Stirring is continued at 80° C. for 10 minutes until the catalyst is fully dispersed. To the stirred mixture is then added 106.0 parts of epichlorohydrin over 1 hour at 80–85° C. Once addition is complete, the reaction mixture is cooled to 30° C., treated with 19.4 parts dimethylamine, in the form of a 60% aqueous solution, and heated to 90° C. for 1 hour. The reaction mixture is cooled to 55° C., and the pH adjusted to 8 using a 30% aqueous solution of sodium hydroxide. After 1 hour at 55–60° C., the reaction mixture is treated with 17.5 parts ethanolamine and heated at 95–100° C. and pH 8 (30% sodium hydroxide) for a further 2 hours to give a water-miscible, cationic intermediate (3c).

The intermediate is stirred at 50–60° C. and treated with 39.4 parts optical brightener precursor of formula (2a), in the form of a 30% aqueous suspension, and 5.9 parts sodium bicarbonate. The reaction mixture is heated to reflux for 4 hours to give an aqueous solution of the amphoteric brightener 4 which can be used as is.

Application Example A

Sizing solutions are prepared by adding a pre-determined amount of the brightener solution to a stirred aqueous solution of a cationic starch (Chargemaster™ R467 from Grain Processing Corporation, Iowa) and a 40% aqueous solution of low molecular mass poly(diallyidimethylammonium chloride) at 60° C. The solution is diluted with water to a starch concentration of 5% and a poly(diallyidimethylammonium chloride) concentration of 2.5%, then allowed to cool.

The sizing solution is poured between the moving rollers of a laboratory size-press and applied to a commercial 75 g/m$^2$ neutral-sized white paper base sheet. The treated paper is dried for 5 minutes at 70° C. in a flat bed drier. The dried paper is allowed to condition, then measured for CIE Whiteness on a calibrated Elrepho spectrophotometer.

A comparison between amphoteric optical brightener 1 and optical brightener 5 of formula

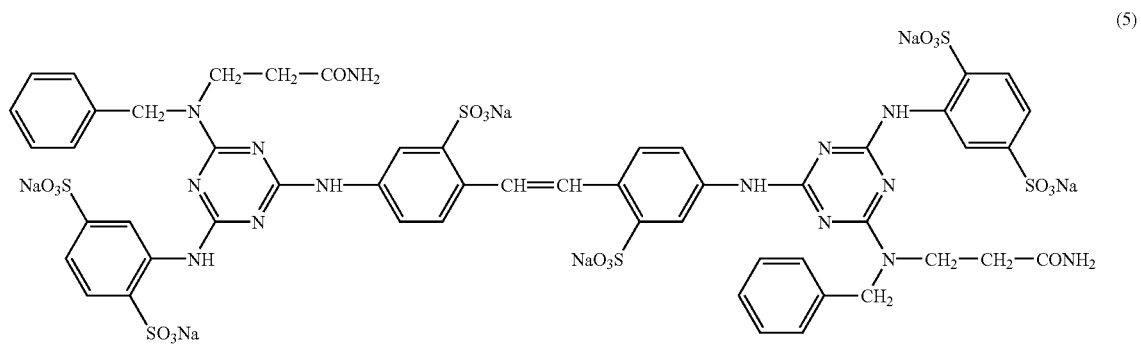

(5)

representative of the state-of-the-art, demonstrates the improved performance of the compound of the invention in a strongly cationic size.

| | CIE whiteness | |
|---|---|---|
| Concentration in mmol/kg | Amphoteric Optical Brightener 1 | Optical Brightener 5 |
| 0 | 81.8 | 81.8 |
| 1.25 | 93.1 | 94.1 |
| 2.5 | 96 | 93.4 |
| 5.0 | 100.5 | 89 |
| 7.5 | 100.8 | 87.8 |

Analogously as the optical brightener 1, each of the optical brighteners 2, 3 and 4 can be used in Application Example A.

Application Example B

Sizing solutions are prepared by adding a pre-determined amount of the brightener solution to a stirred aqueous solution of an anionic oxidised potato starch (Perfectamyl™ A4692) at 60° C. The solution is diluted with water to a starch concentration of 5%, then allowed to cool.

Brightened papers were then prepared as descibed in Application Example A.

A comparison between the amphoteric optical brightener 2 and optical brightener 5, representative of the state-of-the-art, demonstrates the improved performance of the compound of the invention in an anionic size.

| | CIE whiteness | |
|---|---|---|
| Concentration in mmol/kg | Amphoteric Optical Brightener 2 | Optical Brightener 5 |
| 0 | 81.7 | 81.7 |
| 1.25 | 94.5 | 92.1 |
| 2.5 | 101.4 | 99.3 |
| 5.0 | 109 | 105.9 |
| 7.5 | 112.8 | 109.8 |
| 10.0 | 115.5 | 112.8 |

Analogously as the optical brightener 2, each of the optical brighteners 1, 3 and 4 can be used in Application Example A.

Production Examples of White Pigments (WP)

10 parts of a filler or pigment ($M_X$) are mixed in a suitable vessel with 300 parts of water and x parts of cationic product (W) in the form of aqueous concentrate produced in the above Examples are added thereto with the aid of further 80 parts of water and the mixture is stirred during 5 minutes at 400 rpm and then suction-filtered through a glass fibre paper filter. The moist filter pad is transferred to a drying oven and dried at 30° C. The dried product is then ground to a fine powder of average particle size of 1 µm with >80%<2 µm and <2%>10 µm.

x=0.1, 0.2, 0.3, 0.4, 0.5, 0.6, 0.7 and 0.8.

If desired, before filtering, the product may be treated with an optical brightener.

The dried powder may directly be employed. For measuring the whiteness it may shaped into tablets by means of a tablet press. The tablet may be used for measuring the whiteness, e.g. by means of a spectrophotometer (Minolta CM-3700d).

The following cationically modified pigments ($WP_X$) are produced with the following fillers or pigments ($M_X$):

for ($WP_{X1}$)

($M_{X1}$) Fine, white, high purity calcium carbonate with a density by ISO 787/10 of 2.7, commercially available under the trade name HYDROCARB OG of Plüss-Stauffer AG, Oftringen, Switzerland for ($WP_{X2}$)

($M_{X2}$) Very fine, white, natural microcrystalline calcium carbonate (calcite) slurry with a density of 1.89, commercially available under the trade name HYDROCARB 90M slurry from Omya UK or resp. Croxton and Garry Limited.

for ($WP_{X3}$)

($M_{X3}$) calcium carbonate commercially available under the trade name SNOWCAL 60 from Omya UK or resp. Croxton and Garry Limited.

for ($WP_{X4}$)

($M_{X4}$) Precipitated calcium carbonate commercially available under the trade name HAKUENKA TDD from Omya UK.

for ($WP_{X5}$)

($M_{X5}$) Fine, white, highly refined clay commercially available under the trade name SUPREME from EEC International Ltd.

for ($WP_{X6}$)

($M_{X6}$) Fine, white, highly refined clay commercially available under the trade name SPESWHITE from EEC International Ltd.

for (WP$_{X7}$)

(M$_{X7}$) Fine, white, high purity coating clay commercially available under the trade name SPS from EEC International Ltd.

for (WP$_{X8}$)

(M$_{X8}$) China Clay grade B from EEC International Ltd.

Application Example C

A coating composition is prepared containing 3000 parts of the cationically modified chalk (W$_{X1}$) treated with the product of Example 1, 18 parts cationic dispersing agent, and 600 parts latex (a copolymer of n-butyl acrylate and styrene latex of pH 7.5–8.5, commercially available under the trade name ACRONAL S320D). The solids content is adjusted to 55% by the addition of water. The so prepared coating composition is then applied to a commercial 75 g/m² neutral-sized (with conventional alkyl ketene dimer), bleached paper base sheet, using an automatic wire-wound bar applicator with a standard speed setting and a standard load on the bar. The coated paper is dried for 5 minutes at 70° C. in a hot air flow. The dried paper is allowed to condition, then measured for CIE whiteness on a calibrated Datacolor ELREPHO 2000 spectrophotometer. The measured values show a surprisingly high whiteness degree and yield.

Application Example D 200 g of a pulp suspension (2.5% aqueous suspension of a 50% mixture of bleached soft wood and hard wood pulps beaten to a freeness of about 20°SR) is measured into a beaker and stirred, then 40% filler suspension [80 g of 100 g/liter (W$_{X3}$) in water] is added. After the addition the mixture is stirred for a further 0.5 minutes and then 1.7% (3.4 g) of neutral size is added (typically a dispersion of 2.5 g of Aquapel 360X in water—Aquapel 360X is an alylketene dimer size suspension from Hercules Ltd.). After the addition of the size a retention aid may be added—typically Cartaretin PC. The mixture is then diluted to one liter and the paper sheet is formed on a laboratory sheet former (basically this is a cylinder with a wire gauze at the bottom—the cylinder is partly filled with water, the pulp suspension is added, air is then blown through to ensure the pulp is well dispersed, a vacuum is then applied and the pulp slurry is pulled through the wire to leave a paper sheet, this sheet is removed from the wire and pressed and dried). The sheet is left in a humidity cabinet to achieve equilibrium and then the whiteness is measured using a Datacolor ELREPHO 2000 spectrophotometer. The measured values show a surprisingly high whiteness degree and yield.

Application Example E 200 g of a pulp suspension (2.5% aqueous suspension of a 50% mixture of bleached soft wood and hard wood pulps beaten to a freeness of about 20°SR) is measured into a beaker and stirred and 20% filler suspension [40 g of 100 g/liter of a suspension of (M$_{X8}$) treated with the product of Example 1, in water] is added. After the addition the mixture is stirred for a further 5 minutes and then 2% of rosin size solution is added (typically—'T size 22/30' from Hercules), the mixture is stirred for a further 2 minutes and then 3 ml of alum solution (50 g alum in 1 liter water) are added and the mixture is stirred for a further 2 minutes. The mixture is then diluted to one liter and the paper sheet is formed on a laboratory sheet former. The sheet is left in a humidity cabinet to achieve equilibrium and then the whiteness is measured using a Datacolor ELREPHO 2000 Spectrophotometer. The measured values show a surprisingly high whiteness degree and yield.

Analogously as the product of Example 1, the products of each of Examples 2 3 and 4 are employed in the above Application Examples C, D and E.

The invention claimed is:

1. A water soluble, amphoteric optical brightener compound of the average formula $$X-[Z-Y]_n$$

in which

X is a precursor compound containing the structure of formula (Ib')

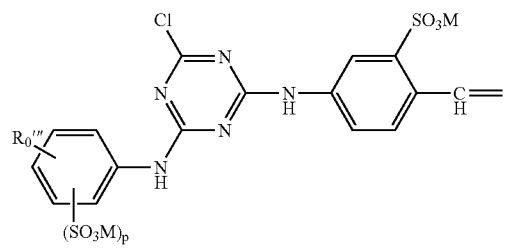

(Ib')

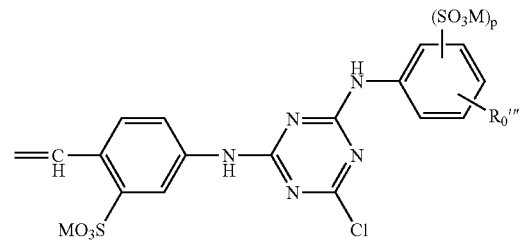

wherein n is from 1 to 2, p is 0, 1 or 2,

R$_0'''$ is hydrogen, methyl, methoxy or chlorine,

M is hydrogen or an alkali metal cation,

Z is a tertiary amino group, covalently linking X to Y, and

Y is the reaction product of epichlorohydrin with a polyfunctional aliphatic alcohol of formula (III')

$$H-(CHOH)_{x3}-H \qquad (III')$$

with x3 being 3 to 6, and a primary, secondary or tertiary mono- or polyamine or mixtures thereof.

2. The optical brightener according to claim 1, wherein p is 1 or 2,

R$_0'''$ is hydrogen,

M is a Sodium cation, n and Z are defined as in claim 1 and

Y is the reaction product of epichlorohydrin with D-sorbitol, glycerol or mixtures thereof and N,N-dimethylethanolamine, ethanolamine, triethylamine, isopropylamine, dimethylamine, N,N,N',N'-tetramethylethylene diamine or mixtures thereof.

3. A process for the production of an amphoteric optical brightener compound according to claim 1, wherein each mole of an optical brightener precursor of Formula (I)

$$X\text{-}(Hal)_m \qquad (I),$$

wherein
X is defined as in claim 1
Hal is halogen, and
m is from 1 to 2,
is condensed with n moles of an amine of Formula (II), $$HZ'\text{-}Y \qquad (II),$$

wherein
Z' is a secondary amino group,
Y is defined as in claim 1, and
n is at least 1.

4. The process according to claim 3, wherein
Hal is chlorine,
m is 2, and
n is 2.